(12) United States Patent
Jiang et al.

(10) Patent No.: US 9,063,119 B2
(45) Date of Patent: *Jun. 23, 2015

(54) METHODS FOR DETECTING VITAMIN C BY MASS SPECTROMETRY

(71) Applicant: Quest Diagnostics Investments Incorporated, Wilmington, DE (US)

(72) Inventors: Qibo Jiang, Los Angeles, CA (US); Richard E Reitz, San Clemente, CA (US); Sum Chan, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/305,897

(22) Filed: Jun. 16, 2014

(65) Prior Publication Data

US 2014/0291502 A1     Oct. 2, 2014

Related U.S. Application Data

(63) Continuation of application No. 14/063,925, filed on Oct. 25, 2013, now Pat. No. 8,759,754, which is a continuation of application No. 13/725,049, filed on Dec. 21, 2012, now Pat. No. 8,569,689, which is a (Continued)

(51) Int. Cl.
| | |
|---|---|
| *H01J 49/04* | (2006.01) |
| *G01N 33/82* | (2006.01) |
| *G01N 33/84* | (2006.01) |

(Continued)

(52) U.S. Cl.
CPC .......... *G01N 33/487* (2013.01); *G01N 30/7233* (2013.01); *G01N 33/82* (2013.01); *G01N 30/84* (2013.01); *H01J 49/26* (2013.01); *H01J 49/004* (2013.01); *H01J 49/0036* (2013.01); *H01J 49/0031* (2013.01)

(58) Field of Classification Search
CPC ... G01N 27/624; G01N 27/64; G01N 27/622; G01N 27/274; G01N 30/06; G01N 30/603; G01N 30/84; G01N 33/487; G01N 33/502; G01N 33/52; G01N 33/55; G01N 33/6848; G01N 33/3893; G01N 33/6896; G01N 33/76; G01N 33/82; C12Q 1/6872; C12Q 1/6874; C12Q 1/26; C12Q 1/28
USPC .................................................. 250/281, 282
See application file for complete search history.

(56) References Cited

U.S. PATENT DOCUMENTS

| | | | | |
|---|---|---|---|---|
| 4,160,696 | A | * | 7/1979 | Wu .................................. 435/25 |
| 5,223,438 | A | * | 6/1993 | Doi ............................... 436/175 |

(Continued)

OTHER PUBLICATIONS

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

(Continued)

*Primary Examiner* — David A Vanore
(74) *Attorney, Agent, or Firm* — Quest Diagnostics, Inc.

(57) ABSTRACT

Provided are methods for determining the amount of vitamin C in a sample using mass spectrometry. The methods generally involve ionizing vitamin C in a sample and detecting and quantifying the amount of the ion to determine the amount of vitamin C in the sample.

18 Claims, 2 Drawing Sheets

Exemplary Chromatograms of Vitamin C and Internal Standard

Related U.S. Application Data continuation of application No. 13/078,792, filed on Apr. 1, 2011, now Pat. No. 8,338,778, which is a continuation of application No. 12/269,862, filed on Nov. 12, 2008, now Pat. No. 7,952,067.

(60) Provisional application No. 61/103,212, filed on Oct. 6, 2008.

(51) Int. Cl.

| | |
|---|---|
| *G01N 33/487* | (2006.01) |
| *G01N 30/72* | (2006.01) |
| *G01N 30/84* | (2006.01) |
| *H01J 49/26* | (2006.01) |
| *H01J 49/00* | (2006.01) |

(56) References Cited

U.S. PATENT DOCUMENTS

| | | | | |
|---|---|---|---|---|
| 5,230,863 | A | * | 7/1993 | Salpeter ..................... 422/67 |
| 5,772,874 | A | | 6/1998 | Quinn et al. |
| 5,795,469 | A | | 8/1998 | Quinn et al. |
| 5,919,368 | A | | 7/1999 | Quinn et al. |
| 5,968,367 | A | | 10/1999 | Quinn et al. |
| 6,107,623 | A | | 8/2000 | Bateman et al. |
| 6,124,137 | A | | 9/2000 | Hutchens et al. |
| 6,204,500 | B1 | | 3/2001 | Whitehouse et al. |
| 6,268,144 | B1 | | 7/2001 | Koster |
| 6,846,654 | B1 | | 1/2005 | Blackburn et al. |
| 7,241,989 | B2 | * | 7/2007 | Miller et al. ............ 250/282 |
| 7,355,170 | B2 | * | 4/2008 | Miller et al. ............ 250/287 |
| 7,576,319 | B2 | * | 8/2009 | Miller et al. ............ 250/282 |
| 7,764,482 | B2 | * | 7/2010 | Lee et al. ................. 361/230 |
| 7,952,067 | B2 | * | 5/2011 | Jiang et al. .............. 250/282 |
| 8,338,778 | B2 | * | 12/2012 | Jiang et al. .............. 250/282 |
| 8,569,689 | B2 | * | 10/2013 | Jiang et al. .............. 250/282 |
| 8,759,754 | B2 | * | 6/2014 | Jiang et al. .............. 250/282 |
| 2002/0119456 | A1 | * | 8/2002 | Ness et al. ................... 435/6 |
| 2009/0090856 | A1 | * | 4/2009 | Grant et al. ............. 250/282 |
| 2009/0104705 | A1 | * | 4/2009 | Stevens et al. ............ 436/63 |
| 2009/0253210 | A1 | * | 10/2009 | Kobold et al. ............ 436/63 |

OTHER PUBLICATIONS

Bradley D.W., et al., "Vitamin C in Plasma: a Comparative Study of the Vitamin Stabilized wiith Trichloroacetic Acid or Metaphosphoric Acid and the Effects of Storage At -70 Degrees, -20 Degrees, 4 Degrees, and 25 Degrees on the Stabilized Vitamin," Clinica Chennica Acta, 1973, vol. 44 (1), pp. 47-52.

Franke A.A., et al., "Vitamin C and Flavonoid Levels of Fruits and Vegetables Consumed in Hawaii," Journal of Food Composition and Analysis, 2004, vol. 17 (1), pp. 1-35.

Gentili A., et al., "Simultaneous Determination of Water-Soluble Vitamins in Selected Food Matrices by Liquid Chromatography/Electrospray Ionization Tandem Mass Spectrometry," Rapid Communications in Mass Spectrometry, 2008, vol. 22 (13), pp. 2029-2043.

Karlsen A., et al., "High-Throughput Analysis of Vitamin C in Human Plasma with the Use of HPLC with Monolithic Column and UV-Protection," Journal of Chromatography B, 2005, vol. 824 (1-2), pp. 132-138.

Karlsen A., et al., "Stability of Whole Blood and Plasma Ascorbic Acid," European Journal of Clinical Nutrition, 2007, vol. 61 (10), pp. 1233-1236.

Konings E.J., et al., "Water-Soluble Vitamins," Journal of AOAC International, 2006, vol. 89 (1), pp. 285-288.

Lundegardh B., et al.,"Impact of Different Green Manures on the Content of S-Alk(en)yl-I-cysteine Sulfoxides and I-Ascorbic Acide in Leek (*Allium* Porrum) ," Journal of Argricultural and Food Chemistry, 2008 vol. 56, pp. 2102-2111.

Merchant M., et al., "Recent Advancements in Surface-Enhanced Laser Desorption/Ionization-Time of Flight-Mass Spectrometry," Electrophoresis, 2000, vol. 21 (6), pp. 1164-1177.

Non-Final Office Action mailed Dec. 16, 2013 for U.S. Appl. No. 14/063,925, filed Oct. 25, 2013.

Non-Final Office Action mailed Apr. 18, 2012 for U.S. Appl. No. 13/078,792 filed Apr. 1, 2011.

Notice of Allowance mailed Jan. 13, 2011 for U.S. Appl. No. 12/269,862 filed Nov. 12, 2008.

Notice of Allowance mailed Aug. 27, 2012 for U.S. Appl. No. 13/078,792, filed Apr. 1, 2011.

Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.

Robb D.B., et al., "Atmospheric Pressure Photoionization: An Ionization Method for Liquid Chromatography- Mass Spectrometry," Analytical Chemistry, 2000, vol. 72 (15), pp. 3653-3659.

Salminen I., et al., "Plasma Ascorbic Acid Preparation and Storage for Epidemiological Studies Using TCA Precipitation," Clinical Biochemistry, 2008, vol. 41 (9), pp. 723-727.

Tai A., et al., "An Isocratic HPLC Method for the Simultaneous Determination of Novel Stable Lipophilic Ascorbic Acid Derivatives and their Metabolites," Journal of Chromatography B, 2006, vol. 840 (1), pp. 38-43.

Walker P.G., et al., "A High Throughput Monolithic HPLC Method for Rapid Vitamin C Phenotyping of Berry Fruit," Phytochemical Analysis , 2006, vol. 17 (5), pp. 284-290.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Zafra-Gomez A., et al., "Simultaneous Determination of Eight Water-Soluble Vitamins in Supplemented Foods by Liquid Chromatography," Journal of Agricultural and Food Chemistry, 2006, vol. 54 (13), pp. 4531-4536.

Zimmer D., et al., "Comparison of Turbulent-Flow Chromatography with Automated Solid-Phase Extraction in 96-Well Plates and Liquid-Liquid Extraction Used As Plasma Sample Preparation Techniques for Liquid Chromatography-Tandem Mass Spectrometry," Journal of Chromatography A, 1999, vol. 854, pp. 23-35.

\* cited by examiner

Figure 1. Exemplary Chromatograms of Vitamin C and Internal Standard
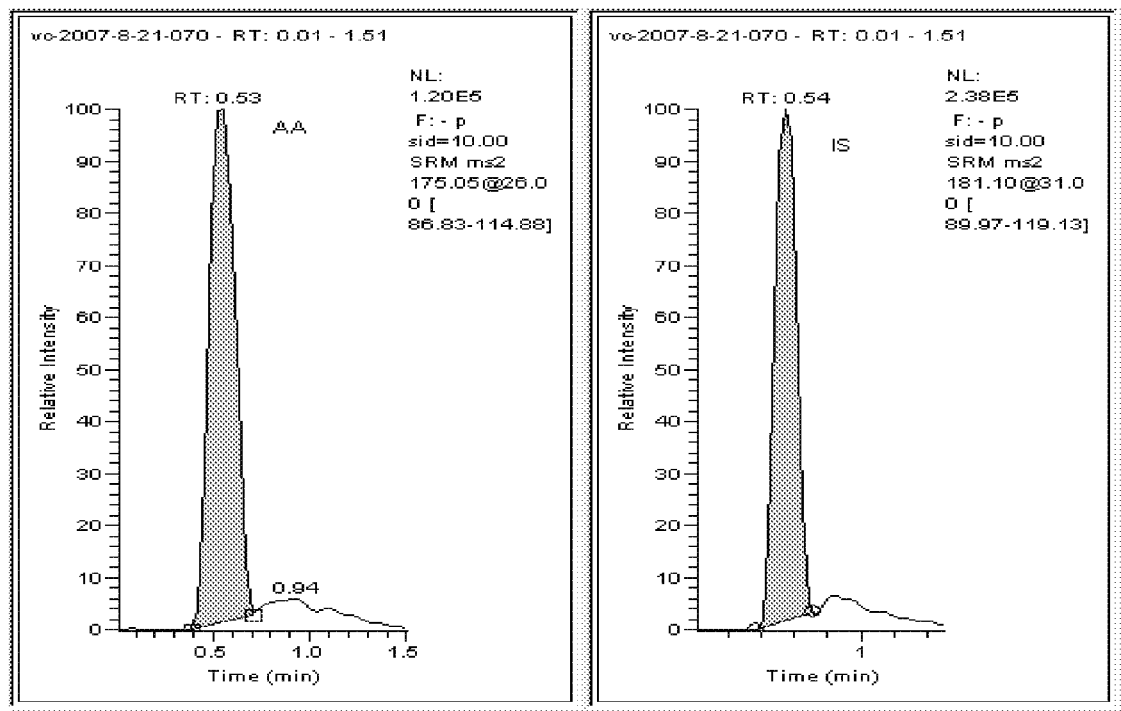

Figure 2. Linearity – Typical Calibration Curve
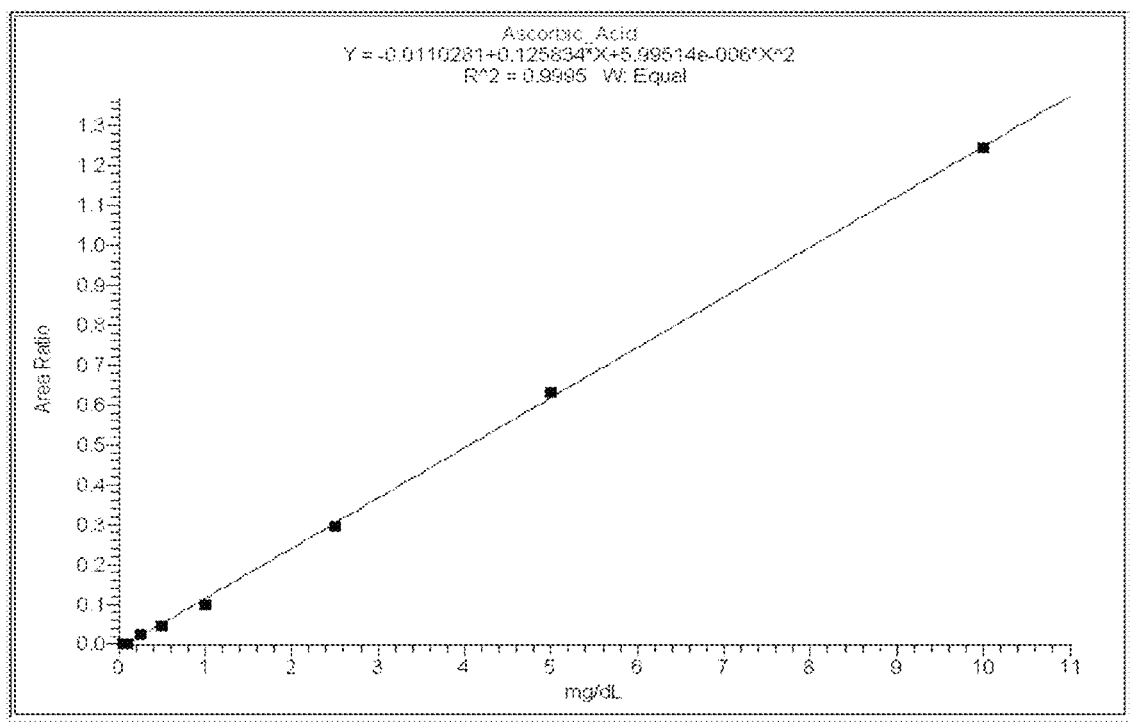

METHODS FOR DETECTING VITAMIN C BY MASS SPECTROMETRY

CROSS-REFERENCE TO RELATED PATENT APPLICATIONS

This application is a continuation of U.S. application Ser. No. 14/063,925, filed Oct. 25, 2013, which is a continuation of U.S. application Ser. No. 13/725,049, filed Dec. 21, 2012, now U.S. Pat. No. 8,569,689, which is a continuation of U.S. application Ser. No. 13/078,792, filed Apr. 1, 2011, now U.S. Pat. No. 8,338,778, which is a continuation of U.S. application Ser. No. 12/269,862, filed Nov. 12, 2008, now U.S. Pat. No. 7,952,067, which claims benefit of U.S. Provisional Application No. 61/103,212, filed Oct. 6, 2008, each of which is incorporated by reference herein in its entirety.

FIELD OF THE INVENTION

The invention relates to the detection of Vitamin C. In a particular aspect, the invention relates to methods for detecting Vitamin C by mass spectrometry.

BACKGROUND OF THE INVENTION

The following description of the background of the invention is provided simply as an aid in understanding the invention and is not admitted to describe or constitute prior art to the invention.

Vitamin C [2-oxo-L-threo-hexono-1,4-lactone2,3-enediol] or L-ascorbic acid is a water-soluble vitamin and essential nutrient for humans. It is essential in the formation of collagen, which is required for normal growth and development as well as tissue repair in all parts of the body. Vitamin C also functions as an antioxidant that blocks the damage caused by free radicals and directly reduces toxic chemicals and pollutants.

As humans do not produce vitamin C in the body, it is primarily obtained from dietary sources such as fruits and vegetables. Lack of dietary vitamin C may result in vitamin C deficiency. Severe vitamin C deficiency, also know as "scurvy," leads to the formation of liver spots on skin, spongy gums, and bleeding from mucous membranes, or even death.

Currently, vitamin C is not only used as a dietary supplement, but also as an adjunct therapy for some viral infections and terminal cancers. The recommended daily intake of vitamin C for adults to prevent deficiency is 75 mg for females and 90 mg for males, both with a tolerable upper level of 2,000 mg. For therapeutic usage in detoxification and cancer therapy, vitamin C is given intravenously at much higher doses. Although vitamin C toxicity is rare clinically, relatively high doses of oral intake may lead to stomach upset and diarrhea.

Assays for vitamin C blood levels have been developed and are used by patients and physicians to evaluate nutritional status or to optimize therapeutic dosages.

SUMMARY OF THE INVENTION

The present invention provides methods for detecting the amount of vitamin C in a sample by mass spectrometry, including tandem mass spectrometry.

In one aspect, methods are provided for determining the amount of vitamin C in a test sample. Methods of this aspect include: (a) ionizing vitamin C from the test sample to produce one or more vitamin C ions detectable by mass spectrometry; and (b) detecting the amount of the vitamin C ion(s) by mass spectrometry. Once the amount of the one or more vitamin C ions is measured, the amount of vitamin C ion(s) is related to the amount of vitamin C in the test sample. In these methods, the one or more vitamin C ions detectable by tandem mass spectrometry include one or more ions selected from the group consisting of ions with a mass/charge ratio of 175.05±0.5, 114.85±0.5, and 86.85±0.5. In some embodiments, the mass spectrometry is tandem mass spectrometry. In some embodiments, the methods further comprise purifying vitamin C in the test samples prior to mass spectrometry. In related embodiments, said purifying comprises purifying by liquid chromatography. In further related embodiments, the liquid chromatography is high performance liquid chromatography (HPLC). In some embodiments, purifying vitamin C comprises one or more purification steps prior to liquid chromatography. In related embodiments, the one or more purification steps preceding liquid chromatography may include protein precipitation. In some embodiments, the test sample is body fluid; preferably plasma or serum. In some embodiments, the step of ionizing vitamin C includes generating a precursor ion with a mass/charge ratio of 175.05±0.5, and generating one or more fragment ions selected from the group consisting of ions with a mass/charge ratio of 114.85±0.5, and 86.85±0.5. In some embodiments, a stabilizing agent may be added to the test sample prior to mass spectrometry. In related embodiments, the stabilizing agent is trichloroacetic acid (TCA). In some embodiments, the method has a lower limit of quantitation within the range of 10.0 mg/dL and 0.1 mg/dL, inclusive. In some embodiments, the amount of one or more vitamin C ions determined by mass spectrometry is related to the presence or amount of vitamin C in the test sample by comparison to an internal standard; preferably $^{13}C_6$-L-ascorbic acid.

In a second aspect, methods are provided for determining the amount of vitamin C in a body fluid sample by mass spectrometry. Methods of this aspect include: (a) purifying vitamin C in a body fluid sample; (b) ionizing vitamin C from the body fluid sample to produce one or more vitamin C ions detectable by mass spectrometry; and (c) detecting the amount of the vitamin C ion(s) by mass spectrometry. In these methods, the amount of the vitamin C ion(s) determined by mass spectrometry is related to the amount of vitamin C in the test sample. In some embodiments, the mass spectrometry is tandem mass spectrometry. In some embodiments, the body fluid samples are purified by liquid chromatography. In related embodiments, the liquid chromatography may be high performance liquid chromatography (HPLC). In some embodiments, the step of purifying vitamin C in a test sample includes one or more purification steps prior to liquid chromatography. In related embodiments, the one or more purification steps preceding liquid chromatography may include protein precipitation. In some embodiments, the test sample is plasma or serum. In some embodiments, the vitamin C ions detectable by mass spectrometry include one or more ions selected from the group consisting of ions with a mass/charge ratio of 175.05±0.5, 114.85±0.5, and 86.85±0.5. In some embodiments, the step of ionizing vitamin C includes generating a precursor ion with a mass/charge ratio of 175.05±0.5, and generating one or more fragment ions selected from the group consisting of ions with a mass/charge ratio of 114.85±0.5, and 86.85±0.5. In some embodiments, a stabilizing agent may be added to the test sample prior to mass spectrometry; preferably prior to purifying the test sample. In related embodiments, the stabilizing agent is trichloroacetic acid (TCA). In some embodiments, the method has a lower limit of quantitation within the range of 10.0 mg/dL and 0.1 mg/dL, inclusive. In some embodiments, the amount of one or more vitamin C ions determined by mass spectrometry is related to the presence or amount of vitamin C in the test sample by comparison to an internal standard; preferably $^{13}C_6$-L-ascorbic acid.

In at third aspect, methods are provided for determining the amount of vitamin C in a body fluid sample by tandem mass spectrometry. Methods of this aspect include: (a) purifying vitamin C from a body fluid sample by liquid chromatography; (b) generating a precursor ion of vitamin C having a mass/charge ratio of 175.05±0.5; (c) generating one or more fragment ions of the precursor ion selected from the group of fragment ions having a mass/charge ratio of 114.85±0.5, and 86.85±0.5; and (d) detecting the amount of one or more of the ions generated in step (b) or (c) or both and relating the determined ions to the amount of vitamin C in the body fluid sample. In some embodiments, the method has a lower limit of quantitation within the range of 10.0 mg/dL and 0.1 mg/dL, inclusive. In some embodiments, liquid chromatography is high performance liquid chromatography (HPLC). In some embodiments, the step of purifying vitamin C in a body fluid sample includes one or more purification steps prior to liquid chromatography. In related embodiments, the one or more purification steps preceding liquid chromatography may include protein precipitation. In some embodiments, the test sample is plasma or serum. In some embodiments, a stabilizing agent may be added to the test sample prior to mass spectrometry; preferably prior to purifying the test sample. In related embodiments, the stabilizing agent is trichloroacetic acid (TCA). In some embodiments, the method has a lower limit of quantitation within the range of 10.0 mg/dL and 0.1 mg/dL, inclusive. In some embodiments, the amount of one or more vitamin C ions determined by mass spectrometry is related to the presence or amount of vitamin C in the test sample by comparison to an internal standard; preferably $^{13}C_6$-L-ascorbic acid.

Methods of the present invention involve the combination of liquid chromatography with mass spectrometry. In preferred embodiments, the liquid chromatography is HPLC. One preferred embodiment utilizes HPLC alone or in combination with one or more purification methods such as for example HTLC or protein precipitation and filtration, to purify vitamin C in samples. In another preferred embodiment, the mass spectrometry is tandem mass spectrometry (MS/MS).

In certain preferred embodiments of the methods disclosed herein, mass spectrometry is performed in negative ion mode. Alternatively, mass spectrometry is performed in positive ion mode. Various ionization sources, including for example atmospheric pressure chemical ionization (APCI) or electrospray ionization (ESI), may be used in embodiments of the present invention. In certain preferred embodiments, vitamin C is measured using APCI in negative mode.

In preferred embodiments, vitamin C ions detectable in a mass spectrometer are selected from the group consisting of negative ions with a mass/charge ratio (m/z) of 175.05±0.50, 114.85±0.50, and 86.85±0.50. In particularly preferred embodiments, a vitamin C precursor ion has m/z of 175.05±0.50, and one or more fragment ions are selected from the group consisting of ions having m/z of 114.85±0.50 and 86.85±0.50.

In preferred embodiments, a separately detectable internal vitamin C standard is provided in the sample, the amount of which is also determined in the sample. In these embodiments, all or a portion of both the endogenous vitamin C and the internal standard present in the sample is ionized to produce a plurality of ions detectable in a mass spectrometer, and one or more ions produced from each are detected by mass spectrometry.

A preferred internal vitamin C standard is $^{13}C_6$-L-ascorbic acid. In preferred embodiments, the internal vitamin C standard ions detectable in a mass spectrometer are selected from the group consisting of negative ions with m/z of 181.10±0.50, 119.10±0.50, and 90.00±0.50. In particularly preferred embodiments, a precursor ion of the internal vitamin C standard has m/z of 181.10±0.50; and one or more fragment ions are selected from the group consisting of ions having m/z of 119.10±0.50, and 90.00±0.50.

In preferred embodiments, the presence or amount of the vitamin C ion is related to the presence or amount of vitamin C in the test sample by comparison to a reference such as $^{13}C_6$-L-ascorbic acid.

In certain preferred embodiments, the lower limit of quantitation (LLOQ) of vitamin C is within the range of 10.0 mg/dL and 0.1 mg/dL, inclusive; preferably within the range of 5.0 mg/dL and 0.1 mg/dL; preferably within the range of 2.5 mg/dL and 0.1 mg/dL; preferably within the range of 1.0 mg/dL and 0.1 mg/dL; preferably within the range of 0.50 mg/dL and 0.1 mg/dL; preferably within the range of 0.40 mg/dL and 0.1 mg/dL; preferably within the range of 0.30 mg/dL and 0.1 mg/dL; preferably within the range of 0.20 mg/dL and 0.1 mg/dL; preferably about 0.1 mg/dL.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected vitamin C parent or daughter ions by mass spectrometry. Relative reduction as this term is used does not require that any substance, present with the analyte of interest in the material to be purified, is entirely removed by purification.

As used herein, the term "test sample" refers to any sample that may contain vitamin C. As used herein, the term "body fluid" means any fluid that can be isolated from the body of an individual. For example, "body fluid" may include blood, plasma, serum, bile, saliva, urine, tears, perspiration, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and high turbulence liquid chromatography (HTLC).

As used herein, the term "high performance liquid chromatography" or "HPLC" refers to liquid chromatography in which the degree of separation is increased by forcing the mobile phase under pressure through a stationary phase on a support matrix, typically a densely packed column.

As used herein, the term "high turbulence liquid chromatography" or "HTLC" refers to a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J. Chromatogr.* A 854: 23-35 (1999); see also, U.S. Pat. Nos. 5,968,367, 5,919,368, 5,795,469, and 5,772,874, which further explain HTLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 35 µm. As used in this context, the term "about" means ±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means ±10%. In a preferred embodiment the analytical column contains particles of about 3.5 µm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "limit of quantification", "limit of quantitation" or "LOQ" refers to the point where measurements become quantitatively meaningful. The analyte response at this LOQ is identifiable, discrete and reproducible with a relative standard deviation (RSD %) of 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the LOQ.

As used herein, an "amount" of vitamin C in a body fluid sample refers generally to an absolute value reflecting the mass of vitamin C detectable in volume of body fluid. However, an amount also contemplates a relative amount in comparison to another vitamin C amount. For example, an amount of vitamin C in a body fluid can be an amount which is greater than a control or normal level of vitamin C normally present.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 1 shows exemplary chromatograms of vitamin C and $^{13}C_6$-L-ascorbic acid (internal standard). Details are discussed in Example 3.

FIG. 2 shows the linearity of the quantitation of vitamin C in serially diluted stock samples using an LC-MS/MS assay. Details are described in Example 6.

DETAILED DESCRIPTION OF THE INVENTION

Methods for detecting vitamin C using liquid chromatography coupled with various detection means have been described in the art. For example Tai A, et al., J Chromatogr B 2006, 840:38-43; Zafra-Gómez A, et al., J Agric Food Chem 2006, 54:4531-6; Walker, P, et al., Phytochem Anal 2006, 17:284-90; Karlsen A, et al., Eur J Clin Nutr 2007, 61:1233-6; and Lundegårdh B, et al., J Agric Food Chem 2008, 56:2102-11 describe detection of vitamin C using high performance liquid chromatography and ultraviolet/visible light (UV-Vis) absorbance. Methods to detect vitamin C in food matrices by liquid chromatography/coulometric detection are disclosed in Franke, A., et al., J Food Comp Anal. 2004, 17:1-35. Methods to detect vitamin C in plasma by high performance liquid chromatography/electrochemical detection are disclosed in Salminen, I., et al., Clin Biochem 2008, 41:723-7. A method to detect vitamin C in food matrices with high performance liquid chromatography/tandem mass spectrometry by observing a mass transition from a precursor ion with a mass to charge ratio of 177 to fragment ions with mass to charge ratios of 141 and 95 is disclosed in Gentili, et al., Rapid Commun Mass Spectrom 2008, 22:2029-43.

Methods of the present invention are described for measuring the amount of vitamin C in a sample. More specifically, mass spectrometric methods are described for detecting and quantifying vitamin C in a test sample. The methods may utilize liquid chromatography (LC), most preferably HPLC, to perform a purification of selected analytes, and combine this purification with unique methods of mass spectrometry (MS), thereby providing a high-throughput assay system for detecting and quantifying vitamin C in a test sample. The preferred embodiments are particularly well suited for application in large clinical laboratories for automated vitamin C assay. The methods provided are accomplished with decreased vitamin C degradation through sample treatment and preparation.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Particularly preferred samples include bodily fluids such as blood, plasma, serum, saliva, cerebrospinal fluid, or a tissue sample. Such samples may be obtained, for example, from a patient; that is, a living person, male or female, presenting oneself in a clinical setting for diagnosis, prognosis, or treatment of a disease or condition. The test sample is preferably obtained from a patient, for example, blood serum or plasma. Vitamin C in blood serum or plasma is very temperature and light sensitive, so in order to avoid irreversible degradation, samples should be protected from light and placed under dry ice or ultra-low refrigeration and quickly thawed just prior to use. A sample volume of about 2 mL is preferred; however, samples of about 1 mL can be analyzed.

In some embodiments of the present invention, test samples may also be treated prior to mass spectrometry with a stabilizing reagent to slow photo and thermal degradation; preferably prior to purification. In especially preferred embodiments, the stabilizing reagent is the well-known trichloroacetic acid (TCA). See for example, Bradley, et al., Clinica Chemica Acta 1973, 44:47-52. Treatment of test samples with a stabilizing reagent is especially useful in preparing multiple test samples for automated analysis. Multiple test samples, for example 96 samples, each in a well of a 96-well plate, can be prepared for automated analysis by using a stabilizing reagent.

The present invention contemplates kits for an vitamin C quantitation assay. A kit for an vitamin C quantitation assay of the present invention may include a kit comprising trichloroacetic acid (TCA) and an internal standard, in amounts sufficient for at least one assay. Typically, the kits will also include instructions recorded in a tangible form (e.g., contained on paper or an electronic medium) for using the packaged reagents for use in a measurement assay for determining the amount of vitamin C.

Calibration and QC pools for use in embodiments of the present invention can be prepared using "stripped" plasma or serum (stripped of vitamin C): for example, analyte-stripped, defibrinated and delipidized plasma/serum. All sources of human or non-human plasma or stripped serum should be checked to ensure that they do not contain measurable amounts of vitamin C.

Sample Preparation for Mass Spectrometry

Typically, frozen test samples (including controls) are thawed rapidly and kept protected from light exposure to minimize vitamin C degradation. Internal standard may be added to the test samples once they are thawed.

The samples may then be prepared for mass spectrometry by liquid-liquid or solid-phase extraction, and/or treatment with a stabilizing reagent. Various methods may be used to enrich vitamin C relative to other components in the sample (e.g. protein) prior mass spectrometry, including for example, liquid chromatography, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Protein precipitation is one preferred method of preparing a test sample, especially a biological test sample, such as serum or plasma. Such protein purification methods are well known in the art, for example, Polson et al., Journal of Chromatography B 785:263-275 (2003), describes protein precipitation techniques suitable for use in methods of the present invention. Protein precipitation may be used to remove most of the protein from the sample leaving vitamin C in the supernatant. The samples may be centrifuged to separate the liquid supernatant from the precipitated proteins; alternatively the samples may be filtered, for example through a glass fiber filter, to remove precipitated proteins. The resultant supernatant or filtrate may then be applied directly to mass spectrometry analysis; or alternatively to liquid chromatography and subsequent mass spectrometry analysis. In certain embodiments, the use of protein precipitation such as for example, methanol protein precipitation, may obviate the need for high turbulence liquid chromatography (HTLC) or other on-line extraction prior to mass spectrometry or HPLC and mass spectrometry.

Accordingly, in some embodiments, the method involves (1) performing a protein precipitation of the sample of interest; and (2) loading the supernatant directly onto the LC-mass spectrometer without using on-line extraction or high turbulence liquid chromatography (HTLC).

In some embodiments, HTLC, alone or in combination with one or more purification methods, may be used to purify vitamin C prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures may be linked in an automated fashion, the requirement for operator involvement during the purification of the analyte can be minimized. This feature may result in savings of time and costs, and eliminate the opportunity for operator error.

According to preferred embodiments, the method involves adding a stabilizing reagent, such as for example trichloroacetic acid (TCA), to each sample prior to mass spectrometry, for example prior to one or more purification steps, for example prior to storage. In some embodiments, TCA may be added to each sample after protein precipitation, but prior to liquid chromatography.

One means of sample purification that may be used prior to mass spectrometry is liquid chromatography (LC). Liquid chromatography, including high-performance liquid chromatography (HPLC), relies on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select HPLC instruments and columns that are suitable for use with vitamin C. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-18 bonded groups. The chromatographic column includes an inlet port for receiving a sample directly or indirectly from coupled SPE column and an outlet port for discharging an effluent that includes the fractionated sample.

In one embodiment, the sample may be applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a hydrophobic column chromatographic system. In certain preferred embodiments, a C18 analytical column (e.g., a Zorbax SB-C18 analytical column from Agilent Technologies (3.5 µm particle size, 15×4.6 mm), or equivalent) is used. In certain preferred embodiments, HTLC and/or HPLC are performed using HPLC Grade 0.1% aqueous formic acid and 100% acetonitrile as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

Detection and Quantitation by Mass Spectrometry

In various embodiments, vitamin C present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, vitamin C is ionized by atmospheric pressure chemical ionization (APCI) in negative mode. In related preferred embodiments, vitamin C ion is in a gaseous state and the inert collision gas is argon or nitrogen; preferably argon.

In mass spectrometry techniques generally, after the sample has been ionized the positively charged or negatively charged ions thereby created may be analyzed to determine a mass-to-charge ratio. Suitable analyzers for determining mass-to-charge ratios include quadrupole analyzers, ion traps analyzers, magnetic and electric sector analyzers, and time-of-flight analyzers. The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of vitamin C. Methods of generating and using such standard curves are well known in the art and one of ordinary skill is capable of selecting an appropriate internal standard.

For example, an isotopically labeled vitamin C may be used as an internal standard; in certain preferred embodiments the standard is $^{13}C_6$-L-ascorbic acid. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, vitamin C is detected and/or quantified using MS/MS as follows. The samples are subjected to liquid chromatography, preferably HPLC; the flow of liquid solvent from the chromatographic column enters the heated nebulizer interface of an MS/MS analyzer; and the solvent/analyte mixture is converted to vapor in the heated tubing of the interface. The analyte (e.g., vitamin C), contained in the nebulized solvent, is ionized by the corona discharge needle of the interface, which applies a large voltage to the nebulized solvent/analyte mixture. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of vitamin C. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD). The fragment ions generated are passed into quadrupole 3 (Q3), where the fragment ions of vitamin C are selected while other ions are eliminated.

The methods may involve MS/MS performed in either positive or negative ion mode; preferably negative ion mode. Using standard methods well known in the art, one of ordinary skill is capable of identifying one or more fragment ions of a particular precursor ion of vitamin C that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of vitamin C. As described above, the relative abundance of a given ion may be converted into an absolute amount of the original analyte, e.g., vitamin C, using calibration standard curves based on peaks of one or more ions of an internal molecular standard, such as $^{13}C_6$-L-ascorbic acid.

The following examples serve to illustrate the invention. These examples are in no way intended to limit the scope of the methods.

EXAMPLES

Example 1

Sample (Plasma and Serum) and Reagent Preparation

Plasma samples were prepared by collecting blood in a light-protected Vacutainer tube with sodium heparin while refrigerated to about 2° C. to 8° C. Samples were then centrifuged (about 2200-2500 rpm, about 800-1000 g) for about 8 to 10 minutes while refrigerated to about 2° C. to 8° C. The resulting plasma was then transferred to dark-brown polypropylene or polyethylene transport tubes to protect the samples from light. The samples were then placed under dry ice or ultra low freezer (i.e., cooled to a temperature of about −65° C. to −75° C.) to protect from degradation. Samples that were not protected from light and samples that were shipped and/or stored at refrigerated (i.e., about 2° C. to 8° C.) or ambient temperatures were not used for analysis. Additionally, samples that exhibited gross hemolysis and/or lipemia were also excluded.

Serum samples were prepared by collecting blood in a light-protected Vacutainer tube with no additives and allowed to clot for 20 to 30 minutes while refrigerated to about 2° C. to 8° C. The samples were then centrifuged (about 2200-2500 rpm, about 800-1000 g) for about 8 to 10 minutes while refrigerated to about 2° C. to 8° C. The resulting serum was then transferred as above for plasma.

Two vitamin C stock solutions were prepared. A vitamin C stock solution for standards of 100 mg/mL in 1% meta-phosphoric acid was prepared in an amber volumetric flask. A vitamin C stock solution for controls of 10 mg/mL in 1% meta-phosphoric acid was prepared in an amber volumetric flask. Aliquots of stock solutions were protected from light and kept at about −65° C. to −75° C.

$^{13}C_6$-L-ascorbic acid (Quote #184286, MDX, Cerritos, Calif. 90703, or equivalent) was used to prepare a 1.0 mg/mL in methanol $^{13}C_6$-L-ascorbic acid internal standard stock solution, which was used to prepare a 10 mcg/mL internal standard working solution: 1 mL of the $^{13}C_6$-L-ascorbic acid internal standard stock solution was diluted to volume with DI water in a 100 mL volumetric flask.

Example 2

Extraction of Vitamin C from Plasma and Serum Using Liquid Chromatography

Liquid chromatography (LC) samples were prepared by thawing standards, controls, and patient samples to room temperature. Standards, controls, and patient samples were then vortexed for about 5 to 10 seconds.

0.20 mL of each vortexed standard, control, and patient sample was then combined with 1.0 mL of internal standard working solution (10 mcg/mL) and 0.20 mL of 50% aqueous methanol. These mixtures were centrifugally filtered (about 3000-3300 rpm) through a glass fiber filter for about 8 to 10 minutes while refrigerated to about 2° C. to 8° C. 50 μL of 20% aqueous TCA was then added to the each filtrate. Adding the TCA at this point in the procedure helps stabilize vitamin C in the samples. The filtrate/TCA mixtures were then vortexed for about 20 to 25 seconds and poured into the wells of a deep 96-well plate for insertion into an autosampler cooling unit.

Sample injection was performed with a Cohesive Technologies Aria TLX-1 HTLC system operating in laminar flow mode using Aria OS V 1.5 or newer software. Acetonitrile and DI water were used as autosampler wash solutions.

The HTLC system automatically injected 10±4 μL of the above prepared samples into the analytical column (Zorbax SB-C18, 15×4.6 mm, 3.5 μm column). A binary HPLC gradient was applied to the analytical column, to separate vitamin C from other analytes contained in the sample. Mobile phase A was 0.1% aqueous formic acid and mobile phase B was 100% acetonitrile. The HPLC gradient started with no organic mobile phase, ramped to 75% organic mobile phase at approximately 20 seconds, and to 95% at approximately 45 seconds. The analytes eluted off the HPLC column at approximately 30 seconds. The separated sample was then subjected to MS/MS for quantitation of vitamin C.

To determine interference from other vitamins or related compounds, blank sera was spiked with: 10 mcg/mL each of pyridoxine, pyridoxamine, pyridoxal, 4-pyridoxic acid, pyridoxal-5-phosphate, retinol, β-carotene, α-tocopherol, γ-tocopherol, riboflavin, riboflavin-5-phosphate, flavin adenine dinucleotide (FAD), thiamin, thiamin-5-phosphate, thiaminpyrophosphate, pyrithiamin, folic acid, vitamin B12, 1,6-$^{13}$C-ascorbic acid, D-isoascorbic acid, vitamin $D_2$, and vitamin $D_3$; 1 mcg/mL each of 1,25-OH vitamin $D_2$ and 1,25-OH vitamin $D_3$; and 40 mcg/mL each of 25-OH vitamin $D_2$ and 25-vitamin $D_3$. To determine interference from various drugs, blank sera was spiked with 10 mcg/mL each of imipramine, desipramine, amitriptyline, nortriptyline, doxepin, desmethyl doxepin, flouxetine, norflouxetine, maprotiline, clomipramine, desmethyl clomipramine, mycophenolic acid, mycophenolic acid glucuronide, flexainide, amiodarone, desethylamiodarone, hydroxzine, propafenone, lamotrigine, gabapentin, zonisamide, and lidocain. The samples were subject to LC. Of these molecules, the only two that co-eluted with vitamin C were D-isoascorbic acid and 1,6-$^{13}$C-ascorbic acid, but they are synthetic compounds that do not naturally appear in the human body. Further, vitamin C (L-ascorbic acid) and its D-isomer are not inter-convertible even at very high concentrations of 500 mg/dL.

Example 3

Detection and Quantitation of Vitamin C by MS/MS

MS/MS was performed using a Finnigan TSQ Quantum Ultra MS/MS system (Thermo Electron Corporation). The following software programs all from ThermoElectron were used in the Examples described herein: Quantum Tune Master V 1.2 or newer, Xcalibur V 1.4 SR1 or newer, TSQ Quantum 1.4 or newer, and LCQuan V 2.0 with SP1 or newer. Liquid solvent/analyte exiting the analytical HPLC column flowed to the heated nebulizer interface of a Thermo Finnigan MS/MS analyzer. The solvent/analyte mixture was converted to vapor in the heated tubing of the interface. Analytes in the nebulized solvent were ionized by APCI.

Ions passed to the first quadrupole (Q1), which selected ions with a mass to charge ratio of 175.05±0.50 m/z. Ions entering Quadrupole 2 (Q2) collided with argon gas to generate ion fragments, which were passed to quadrupole 3 (Q3) for further selection. Simultaneously, the same process using isotope dilution mass spectrometry was carried out with an internal standard, $^{13}C_6$-L-ascorbic acid. The following mass transitions were used for detection and quantitation during validation on negative polarity.

TABLE 1

Mass Transitions for Vitamin C (Negative Polarity)

| Analyte | Precursor Ion (m/z) | Product Ion (m/z) |
|---|---|---|
| Vitamin C | 175.05 | 86.85 and 114.85 |
| $^{13}C_6$-L-ascorbic acid (internal standard) | 181.10 | 90.00 and 119.10 |

Exemplary chromatograms for vitamin C and $^{13}C_6$-L-ascorbic acid (internal standard) are found in FIG. 1.

Example 4

Intra-Assay and Inter-Assay Precision and Accuracy

Three quality control (QC) pools were prepared from analyte-stripped, defibrinated, and delipidized serum, spiked with vitamin C to a concentration of 0.4, 1.2, and 4.0 dg/mL.

Twenty aliquots from each of the three QC pools were analyzed in a single assay to determine the reproducibility (RSD (%)) of a sample within an assay. The following values were determined:

TABLE 2

Intra-Assay Variation and Accuracy

|  | Level I (0.4 mg/dL) | Level II (1.2 mg/dL) | Level III (4.0 mg/dL) |
|---|---|---|---|
| Mean | 0.37 | 1.21 | 4.04 |
| Standard Deviation | 0.03 | 0.07 | 0.15 |
| RSD (%) | 7.2% | 6.0% | 3.6% |
| Accuracy (%) | 93.1% | 100.9% | 101.0% |

Ten aliquots from each of the three QC pools were assayed over five days to determine the reproducibility (RSD %) between assays. The following values were determined:

TABLE 3

Inter-Assay Variation and Accuracy

|  | Level I (0.4 mg/dL) | Level II (1.2 mg/dL) | Level III (4.0 mg/dL) |
|---|---|---|---|
| Mean | 0.38 | 1.20 | 4.01 |
| Standard Deviation | 0.04 | 0.11 | 0.36 |
| RSD (%) | 9.6% | 9.5% | 8.9% |
| Accuracy (%) | 94.1% | 100.0% | 100.2% |

Example 5

Analytical Sensitivity: Limit of Detection (LOD) and Lower Limit of Quantitation (LLOQ)

The LLOQ is the point where measurements become quantitatively meaningful. The analyte response at this LOQ is identifiable, discrete and reproducible with a relative standard deviation (RSD) of 20% and an accuracy of 85% to 115%. The LLOQ was determined by assaying plasma specimens spiked with vitamin C concentrations of 2.50, 1.00, 0.50, 0.25, 0.10, and 0.05 mg/dL (ten replicates each for five days at each level) then determining the reproducibility. The LOQ for the vitamin C assay was determined to be 0.1 mg/dL The LOD is the point at which a value is beyond the uncertainty associated with its measurement and is defined as three times the RSD of the mean at the LLOQ. To determine the LOQ for the vitamin C assay, the 0.10 mcg/mL vitamin C in plasma standard was run in ten replicates. The results of these assays were statistically analyzed with a mean value of 0.10, a SD of 0.01, and a RSD of 9.3%. Thus, the LOD for the vitamin C assay was 0.03 mg/dL.

Example 6

Assay Reportable Range and Linearity

To establish the linearity of vitamin C detection in the assay, three separate assays, each including one blank assigned as zero standard and eight spiked serum standards at concentrations ranging from 0.05 mg/dL to 10.00 mg/dL, were performed on separate days. A quadratic regression from three consecutive runs yielded coefficient correlations of 0.9987 or greater. A graph showing the linearity of the data is shown in FIG. 2.

Example 7

Matrix Specificity

Matrix specificity was evaluated using human analyte-stripped and delipidized serum (Cat. No. 1131-00, Biocell Labs, Carson, Calif. 90746, or equivalent), deionized (DI) water, 5% albumin, and in-house collected pooled serum to determine whether patient samples could be diluted in a linear fashion. Two serum samples were spiked with high concentrations of vitamin C: one at 25 mg/dL, and the other at 450 mg/dL. The spiked serums were then diluted from 2.5 to 500 times with the above matrices and analyzed. The study indicated that all four matrices could be used for dilution purposes up to 500 fold as long as the concentration after dilution was about 0.5 mg/dL or higher. The results of this study are presented in Table 4.

Example 8

Recovery

A recovery study of vitamin C in spiked DI water and Biocell serum samples was performed (in triplicate for concentrations of 0.10 mg/dL, 0.39 mg/dL, 0.95 mg/dL, 2.70 mg/dL, 5.39 mg/dL, and 11.25 mg/dL). The Biocell serum samples were subjected to the protein precipitation procedure described in Example 2, above. The spiked DI water samples were injected without protein precipitation. Absolute recovery was calculated by dividing the vitamin C concentration detected in the serum samples by the vitamin C concentration detected in the DI water samples. The mean recoveries were 100.0%, 112.8%, 89.5%, 91.1%, 92.9%, and 85.8% respectively. All recoveries were acceptable, i.e., within the range of 80% to 120%.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention

TABLE 4

Matrix Specificity of Serum/Plasma Vitamin C

| | Dilution | Concentration (mg/dL) | Albumin 5% (mg/dL) | DI Water (mg/dL) | Biocell Serum (mg/dL) | In-house Serum (mg/dL) |
|---|---|---|---|---|---|---|
| Day 1 | 0x | 25.00 | | | | |
| | 2.5x | 10.00 | 8.27 | 9.59 | 8.76 | 8.15 |
| | 2.5x | 10.00 | 9.69 | 8.61 | 8.85 | 8.82 |
| | 5x | 5.00 | 4.59 | 4.34 | 4.44 | 4.32 |
| | 5x | 5.00 | 5.17 | 4.69 | 5.08 | 4.36 |
| | 10x | 2.50 | 2.19 | 2.36 | 2.16 | 2.37 |
| | 10x | 2.50 | 2.29 | 2.36 | 2.35 | 2.72 |
| | 25x | 1.00 | 0.86 | 0.83 | 0.88 | 0.88 |
| | 25x | 1.00 | 0.82 | 0.97 | 0.91 | 0.99 |
| | 50x | 0.50 | 0.43 | 0.24 | 0.36 | 0.42 |
| | 50x | 0.50 | 0.54 | 0.30 | 0.39 | 0.47 |
| | 100x | 0.25 | 0.22 | 0.11 | 0.14 | 0.18 |
| | 100x | 0.25 | 0.26 | 0.09 | 0.19 | 0.22 |
| Day 2 | 0x | 450.00 | | | | |
| | 50x | 9.00 | 8.89 | 8.87 | 8.34 | 8.74 |
| | 50x | 9.00 | 8.54 | 8.53 | 7.97 | 8.43 |
| | 100x | 4.50 | 4.30 | 4.02 | 4.08 | 3.87 |
| | 100x | 4.50 | 4.56 | 4.32 | 3.97 | 4.33 |
| | 200x | 2.25 | 2.09 | 2.06 | 1.87 | 2.51 |
| | 200x | 2.25 | 1.97 | 1.91 | 2.09 | 2.20 |
| | 500x | 0.90 | 0.77 | 0.85 | 0.82 | 0.76 |
| | 500x | 0.90 | 0.96 | 0.71 | 0.80 | 0.75 | claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining an amount of vitamin C in a test sample by mass spectrometry, the method comprising:
    (i) ionizing vitamin C in the test sample to generate at least one vitamin C ion detectable by mass spectrometry;
    (ii) determining the amount of the at least one vitamin C ion by mass spectrometry; and
    (iii) using the amount of vitamin C ion(s) from step (ii) to determine the amount of vitamin C in the test sample.

2. The method of claim 1, wherein the ionizing is performed in negative ion mode.

3. The method of claim 1, wherein the ionizing comprises ionizing by atmospheric pressure chemical ionization (APCI) or electrospray ionization (ESI).

4. The method of claim 1, wherein the ionizing comprises generating one or more precursor ion of the vitamin C with a mass/charge ratio of 175.05±0.5.

5. The method of claim 1, wherein the ionizing comprises generating one or more fragment ions comprising a mass/charge ratio of 114.85±0.5 or 86.85±0.5.

6. The method of claim 1, wherein the mass spectrometry is tandem mass spectrometry.

7. The method of claim 1, further comprising purifying vitamin C in the test sample prior to mass spectrometry.

8. The method of claim 7, wherein the purifying comprises purifying with liquid chromatography.

9. The method of claim 8, wherein the liquid chromatography comprises high performance liquid chromatography (HPLC).

10. The method of claim 8, wherein the liquid chromatography comprises high turbulence liquid chromatography (HTLC).

11. The method of claim 7, wherein the purifying comprises protein precipitation.

12. The method of claim 1, wherein the test sample is plasma or serum.

13. The method of claim 1, further comprising adding a stabilizing agent to the test sample prior to (i).

14. The method of claim 1, further comprising adding a stabilizing agent comprising trichloroacetic acid (TCA) to the test sample prior to (i).

15. The method of claim 1, wherein the method has a lower limit of quantitation within a range of 10.0 mg/dL and 0.1 mg/dL, inclusive.

16. A method for diagnosing or prognosing vitamin C deficiency in a patient, the method comprising:
    (i) ionizing vitamin C in a body fluid sample obtained from the patient to generate at least one vitamin C ion detectable by mass spectrometry;
    (ii) determining the amount of the at least one vitamin C ion by mass spectrometry;
    (iii) using the amount of vitamin C ion(s) from step (ii) to determine the amount of vitamin C in the sample;
    wherein vitamin C deficiency is diagnosed or prognosed based on the amount of vitamin C in the sample.

17. A method for diagnosing or prognosing vitamin C toxicity in a patient, the method comprising:
    (i) ionizing vitamin C in a body fluid sample obtained from the patient to generate at least one vitamin C ion detectable by mass spectrometry;
    (ii) determining the amount of the at least one vitamin C ion by mass spectrometry;
    (iii) using the amount of vitamin C ion(s) from step (ii) to determine the amount of vitamin C in the sample;
    wherein vitamin C toxicity is diagnosed or prognosed based on the amount of vitamin C in the sample.

18. A method for diagnosing or prognosing scurvy comprising the steps of claim 16.

* * * * *